(12) United States Patent
Nesbitt

(10) Patent No.: US 9,606,069 B2
(45) Date of Patent: Mar. 28, 2017

(54) METHOD, APPARATUS AND SYSTEM FOR GENERATING MULTIPLE SPATIALLY SEPARATED INSPECTION REGIONS ON A SUBSTRATE

(71) Applicant: KLA-Tencor Corporation, Milpitas, CA (US)

(72) Inventor: Jeremy Nesbitt, San Jose, CA (US)

(73) Assignee: KLA-Tencor Corporation, Milpitas, CA (US)

(*) Notice: Subject to any disclaimer, the term of this patent is extended or adjusted under 35 U.S.C. 154(b) by 151 days.

(21) Appl. No.: 14/314,727

(22) Filed: Jun. 25, 2014

(65) Prior Publication Data

US 2015/0377794 A1 Dec. 31, 2015

(51) Int. Cl.
G01J 4/00 (2006.01)
G01N 21/88 (2006.01)
G01N 21/95 (2006.01)

(52) U.S. Cl.
CPC ..... *G01N 21/8806* (2013.01); *G01N 21/9501* (2013.01); *G01N 2021/8825* (2013.01); *G01N 2021/8848* (2013.01)

(58) Field of Classification Search
CPC ....................................................... G01J 4/00
USPC ........................................................ 356/369
See application file for complete search history.

(56) References Cited

U.S. PATENT DOCUMENTS

| | | | | | |
|---|---|---|---|---|---|
| 3,013,467 | A | * | 12/1961 | Minsky | G02B 21/002 250/215 |
| 5,241,364 | A | * | 8/1993 | Kimura | G02B 21/0068 356/491 |
| 5,355,252 | A | * | 10/1994 | Haraguchi | G02B 21/002 250/201.3 |
| 5,787,061 | A | * | 7/1998 | Tsuchiya | G11B 7/0941 369/118 |
| 6,248,988 | B1 | * | 6/2001 | Krantz | G02B 21/004 250/201.3 |
| 6,429,897 | B2 | * | 8/2002 | Derndinger | G02B 21/0036 250/201.3 |
| 6,674,522 | B2 | * | 1/2004 | Krantz | G01N 21/95607 356/237.1 |
| 6,853,475 | B2 | * | 2/2005 | Feldman | G01N 21/8806 359/285 |
| 7,684,048 | B2 | * | 3/2010 | Meshulach | G01N 21/21 356/495 |

(Continued)

OTHER PUBLICATIONS

PCT Search Report for PCT/US2015/036909, dated Oct. 29, 2015, 4 pages.

*Primary Examiner* — Roy M Punnoose
(74) *Attorney, Agent, or Firm* — Suiter Swantz pc llo

(57) ABSTRACT

Inspection with multiple illumination regions includes generating a primary beam of illumination directed along a primary illumination direction, transmitting a portion of the primary beam of illumination along a first illumination direction, deflecting a portion of the primary beam of illumination along a second illumination direction different from the first illumination direction with one or more angular selection elements, focusing the transmitted portion of the primary beam of illumination onto a first inspection region of the substrate, and focusing the deflected portion of the primary beam of illumination onto a second inspection region of the substrate being spatially separated from the first inspection region.

11 Claims, 12 Drawing Sheets

(56) References Cited

U.S. PATENT DOCUMENTS

| | | | |
|---|---|---|---|
| 2003/0156280 A1* | 8/2003 | Reinhorn | G01N 21/8806 356/237.2 |
| 2004/0207849 A1 | 10/2004 | Nikoonahad et al. | |
| 2005/0122515 A1 | 6/2005 | Borden et al. | |
| 2007/0206187 A1 | 9/2007 | Lundquist et al. | |
| 2012/0026489 A1 | 2/2012 | Zhao et al. | |
| 2012/0307349 A1* | 12/2012 | Arntsen | G02B 27/48 359/327 |
| 2013/0050689 A1 | 2/2013 | Reich et al. | |

* cited by examiner

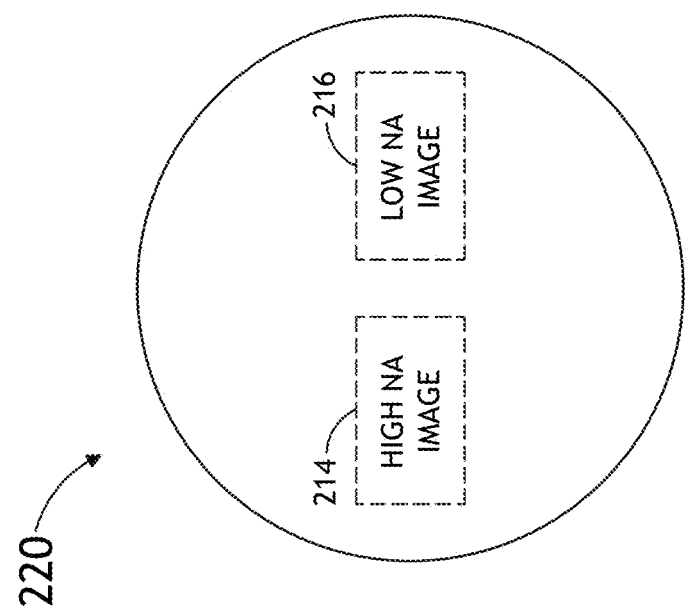
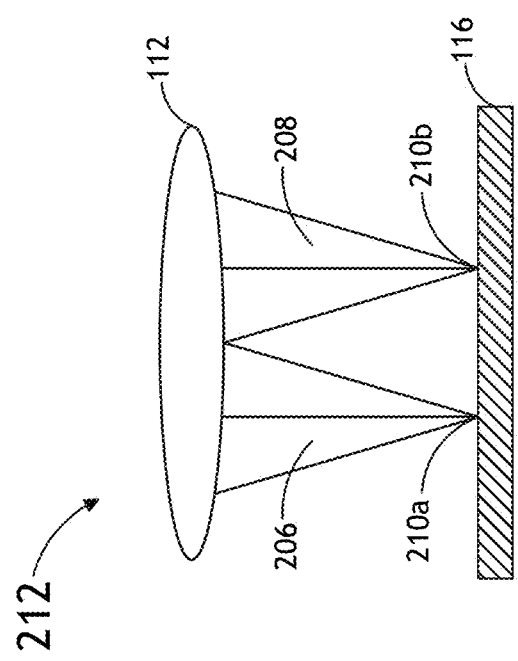
FIG.2B
FIG.2C

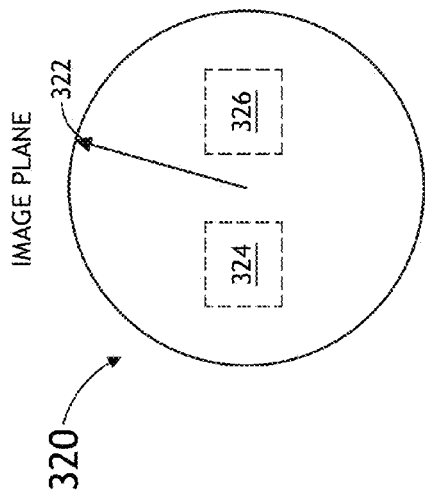
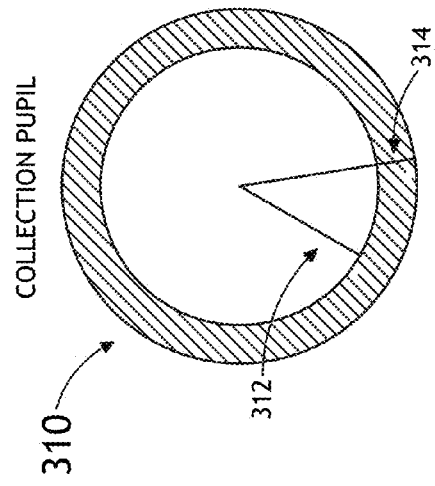
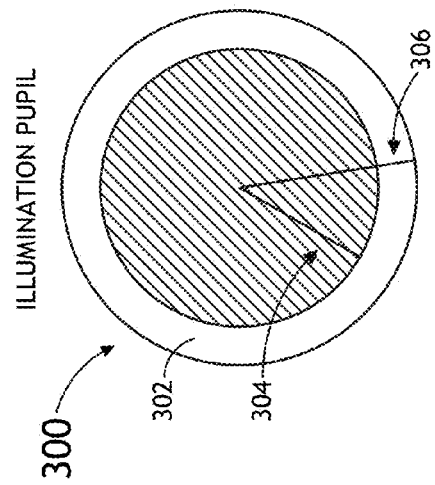

METHOD, APPARATUS AND SYSTEM FOR GENERATING MULTIPLE SPATIALLY SEPARATED INSPECTION REGIONS ON A SUBSTRATE

TECHNICAL FIELD

The present invention generally relates to semiconductor wafer inspection, and, in particular, the generation of multiple spatially separated illumination regions on a semiconductor wafer.

BACKGROUND

As the demand for integrated circuits continues to rise, the need for improved, more efficient processes to inspect wafers continues to grow. One such inspection process uses a flood illumination system. In a flood illumination system, light not used is blocked at some point in the illuminator before it reaches the wafer. Further, one such system may use an aperture to control the angle of incidence or polarization state of the light incident on the wafer. In some cases, multiple inspections are run on the same wafer, with each test applying a different polarization state or angle of incidence. Multi-pass inspections increase the amount of time spent inspecting a single wafer, reducing the overall wafer inspection throughput. Therefore, it would be desirable to provide a system and method for inspecting wafers in a more efficient manner than those identified above.

SUMMARY

An illumination apparatus for generating two or more spatially separated inspection regions on a substrate is disclosed, in accordance with an illustrative embodiment of the present invention. In one illustrative embodiment, the illumination apparatus includes an illumination source for generating a primary beam of illumination directed along a primary illumination direction. In another illustrative embodiment, the illumination apparatus includes one or more polarized illumination deflection elements positioned within the primary beam of illumination configured to direct a first portion of the primary beam having a first polarization along a first illumination direction in order to form a first inspection beam, and further configured to direct a second portion of the primary beam having a second polarization orthogonal to the first polarization along a second illumination direction in order to form a second inspection beam. In another embodiment, the illumination apparatus includes an objective configured to focus the first inspection beam onto a first region of a substrate, and further configured to focus the second inspection beam onto a second region of the substrate, with the first substrate inspection region being spatially separate from the second region.

An illumination apparatus for generating two or more spatially separated inspection regions on a substrate with light of different numerical aperture is disclosed, in accordance with an illustrative embodiment of the present invention. In one illustrative embodiment, the illumination apparatus includes an illumination source for generating a primary beam of illumination directed along a primary illumination direction. In another illustrative embodiment, the illumination apparatus includes one or more angular selection elements positioned within the primary beam of illumination configured to transmit a portion of the primary beam of illumination having a numerical aperture value above a selected value along a first illumination direction in order to form a first inspection beam, and further configured to deflect a portion of the primary beam of illumination having a numerical aperture value below the selected value along a second illumination direction different from the first illumination direction in order to form a second inspection beam. In another embodiment, the illumination apparatus includes an objective configured to focus the transmitted portion of the primary beam of illumination onto a first inspection region of the substrate, and further configured to focus the deflected portion of the primary beam of illumination onto a second inspection region of the substrate, with the first substrate inspection region being spatially separate from the second region.

An illumination apparatus for generating two or more spatially separated inspection regions on a substrate is disclosed, in accordance with an illustrative embodiment of the present invention. In one illustrative embodiment, the illumination apparatus includes an illumination source for generating a primary beam of illumination directed along a primary illumination direction. In another illustrative embodiment, the illumination apparatus includes one or more angular selection elements positioned within the primary beam of illumination configured to transmit a portion of the primary beam of illumination along a first illumination direction in order to form a first inspection beam, and further configured to deflect a portion of the primary beam of illumination along a second illumination direction different from the first illumination direction in order to form a second inspection beam. In another embodiment, the illumination apparatus includes an objective configured to focus the transmitted portion of the primary beam of illumination onto a first inspection region of the substrate, and further configured to focus the deflected portion of the primary beam of illumination onto a second inspection region of the substrate, with the first substrate inspection region being spatially separate from the second region.

An inspection system for inspecting two or more spatially separated regions of a substrate illuminated with light of different polarization is disclosed, in accordance with an illustrative embodiment of the present invention. In one illustrative embodiment, the inspection system includes an illumination source for generating a primary beam of illumination directed along a primary illumination direction. In another illustrative embodiment, the inspection system includes one or more polarized illumination deflection elements positioned within the primary beam of illumination configured to direct a first portion of the primary beam having a first polarization along a first illumination direction in order to form a first inspection beam and further configured to direct a second portion of the primary beam having a second polarization orthogonal to the first polarization along a second illumination direction in order to form a second inspection beam. In another embodiment, the inspection system includes an objective configured to focus the first inspection beam onto a first region of a substrate, and further configured to focus the second inspection beam onto a second region of the substrate, with the first substrate inspection region being spatially separate from the second region. In another embodiment, the inspection system includes a first image sensor configured to collect illumination reflected from the first region of the substrate. In another embodiment, the inspection system includes a second image sensor configured to collect illumination reflected from the second region of the substrate, with the first image sensor and the second image sensor positioned in a common image plane of the inspection system.

An inspection system for inspecting two or more spatially separated inspection regions on a substrate with light of different numerical aperture is disclosed, in accordance with an illustrative embodiment of the present invention. In one illustrative embodiment, the inspection system includes an illumination source for generating a primary beam of illumination directed along a primary illumination direction. In another illustrative embodiment, the inspection system includes one or more angular selection elements positioned within the primary beam of illumination configured to transmit a portion of the primary beam of illumination having a numerical aperture value above a selected value along a first illumination direction in order to form a first inspection beam, and further configured to deflect a portion of the primary beam of illumination having a numerical aperture value below the selected value along a second illumination direction different from the first illumination direction in order to form a second inspection beam. In another embodiment, the inspection system includes an objective configured to focus the transmitted portion of the primary beam of illumination onto a first inspection region of the substrate, and further configured to focus the deflected portion of the primary beam of illumination onto a second inspection region of the substrate, with the first substrate inspection region being spatially separate from the second region. In another embodiment, the inspection system includes a first image sensor configured to collect illumination reflected from the first region of the substrate. In another embodiment, the inspection system includes a second image sensor configured to collect illumination reflected from the second region of the substrate, with the first image sensor and the second image sensor positioned in a common image plane of the inspection system. In another embodiment, the inspection system includes an aperture positioned at or near a collection pupil configured to block light with one or more numerical aperture values conjugate to the numerical aperture value of the portion of the inspection beam transmitted by the angular deflection element from all field points, to image one or more inspection regions in one or more of a brightfield or darkfield mode.

An inspection system for inspecting two or more spatially separated inspection regions on a substrate is disclosed, in accordance with an illustrative embodiment of the present invention. In one illustrative embodiment, the inspection system includes an illumination source for generating a primary beam of illumination directed along a primary illumination direction. In another illustrative embodiment, the inspection system includes one or more angular selection elements positioned within the primary beam of illumination configured to transmit a portion of the primary beam of illumination along a first illumination direction in order to form a first inspection beam, and further configured to deflect a portion of the primary beam of illumination along a second illumination direction different from the first illumination direction in order to form a second inspection beam. In another embodiment, the inspection system includes an objective configured to focus the transmitted portion of the primary beam of illumination onto a first inspection region of the substrate, and further configured to focus the deflected portion of the primary beam of illumination onto a second inspection region of the substrate, with the first substrate inspection region being spatially separate from the second region. In another embodiment, the inspection system includes a first image sensor configured to collect illumination reflected from the first region of the substrate. In another embodiment, the inspection system includes a second image sensor configured to collect illumination reflected from the second region of the substrate, with the first image sensor and the second image sensor positioned in a common image plane of the inspection system.

A method for generating two or more spatially separated inspection regions on a substrate is disclosed, in accordance with an illustrative embodiment of the present invention. In one embodiment, the method may include generating a primary beam of illumination along a primary illumination direction. In another embodiment, the method may include directing a first portion of the primary beam of illumination having a first polarization along a first illumination direction with one or more polarized illumination deflection elements in order to form a first inspection beam. In another embodiment, the method may include directing a second portion of the primary beam of illumination having a second polarization orthogonal to the first polarization along a second illumination direction different from the first illumination direction with the one or more polarized illumination deflection elements in order to form a second inspection beam. In another embodiment, the method may include focusing the first inspection beam having a first polarization onto a first inspection region of the substrate. In another embodiment, the method may include focusing the second inspection beam having a second polarization onto a second inspection region of the substrate being spatially separated from the first inspection region.

A method for generating two or more spatially separated inspection regions on a substrate is disclosed, in accordance with an illustrative embodiment of the present invention. In one embodiment, the method may include generating a primary beam of illumination directed along a primary illumination direction. In another embodiment, the method may include transmitting a portion of the primary beam of illumination having a numerical aperture value above a selected value along a first illumination direction. In another embodiment, the method may include deflecting a portion of the primary beam of illumination having a numerical aperture value below the selected value along a second illumination direction different from the first illumination direction with one or more angular selection elements. In another embodiment, the method may include focusing the transmitted portion of the primary beam of illumination onto a first inspection region of the substrate. In another embodiment, the method may include focusing the deflected portion of the primary beam of illumination onto a second inspection region of the substrate being spatially separated from the first inspection region.

A method for generating two or more spatially separated inspection regions on a substrate is disclosed, in accordance with an illustrative embodiment of the present invention. In one embodiment, the method may include generating a primary beam of illumination directed along a primary illumination direction. In another embodiment, the method may include transmitting a portion of the primary beam of illumination along a first illumination direction. In another embodiment, the method may include deflecting a portion of the primary beam of illumination along a second illumination direction different from the first illumination direction with one or more angular selection elements. In another embodiment, the method may include focusing the transmitted portion of the primary beam of illumination onto a first inspection region of the substrate. In another embodiment, the method may include focusing the deflected portion of the primary beam of illumination onto a second inspection region of the substrate being spatially separated from the first inspection region.

A method for generating two or more spatially separated inspection regions on a substrate is disclosed, in accordance with an illustrative embodiment of the present invention. In one embodiment, the method may include generating a primary beam of illumination directed along a primary illumination direction. In another embodiment, the method may include transmitting a portion of the primary beam of illumination having a numerical aperture value above a selected value along a first illumination direction. In another embodiment, the method may include deflecting a portion of the primary beam of illumination having a numerical aperture value below the selected value along a second illumination direction different from the first illumination direction with one or more angular selection elements. In another embodiment, the method may include focusing the transmitted portion of the primary beam of illumination onto a first inspection region of the substrate. In another embodiment, the method may include focusing the deflected portion of the primary beam of illumination onto a second inspection region of the substrate being spatially separated from the first inspection region. In another embodiment, the method may include directing illumination reflected from the first and second inspection regions through an aperture positioned within a collection pupil configured to block light having a selected range of numerical aperture values to create brightfield and darkfield mode images.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF THE DRAWINGS

The numerous advantages of the disclosure may be better understood by those skilled in the art by reference to the accompanying figures in which:

FIG. 2B is a high-level schematic view of a side view of a substrate plane, in accordance with one embodiment of the present invention.

FIG. 2C is a high-level schematic view of a top view of the image plane of an imaging system implementing an illumination sub-system, in accordance with one embodiment of the present invention.

FIG. 3A is a conceptual view of the illumination pupil in an illumination sub-system, in accordance with one embodiment of the present invention.

FIG. 3B is a conceptual view of the collection pupil in an illumination sub-system, in accordance with one embodiment of the present invention.

FIG. 3C is a conceptual view of the image plane in an illumination sub-system, in accordance with one embodiment of the present invention.

DETAILED DESCRIPTION OF THE INVENTION

Reference will now be made in detail to the subject matter disclosed, which is illustrated in the accompanying drawings.

Referring generally to FIGS. 1A through 3D, illumination sub-systems and inspection systems for generating two or more spatially separated inspection regions on a substrate surface are described in accordance with the present invention.

The present invention is generally directed to the generation of two or more light beams within an illumination sub-system via the selective deflection of one or more portions of light generated by a given light source based on one or more characteristics of the light (e.g., polarization, numerical aperture and the like). The present invention is further directed to directing the two or more light beams onto the surface of a selected substrate, such as a semiconductor wafer. In this regard, the present invention may provide for the simultaneous illumination of two or more regions of a substrate with light of varying characteristics (e.g., polarization, numerical aperture and the like) utilizing a single illumination source. It is recognized that such an approach may improve the efficiency of using illumination (e.g., flood illumination) in a given inspection system.

Figure 1A:
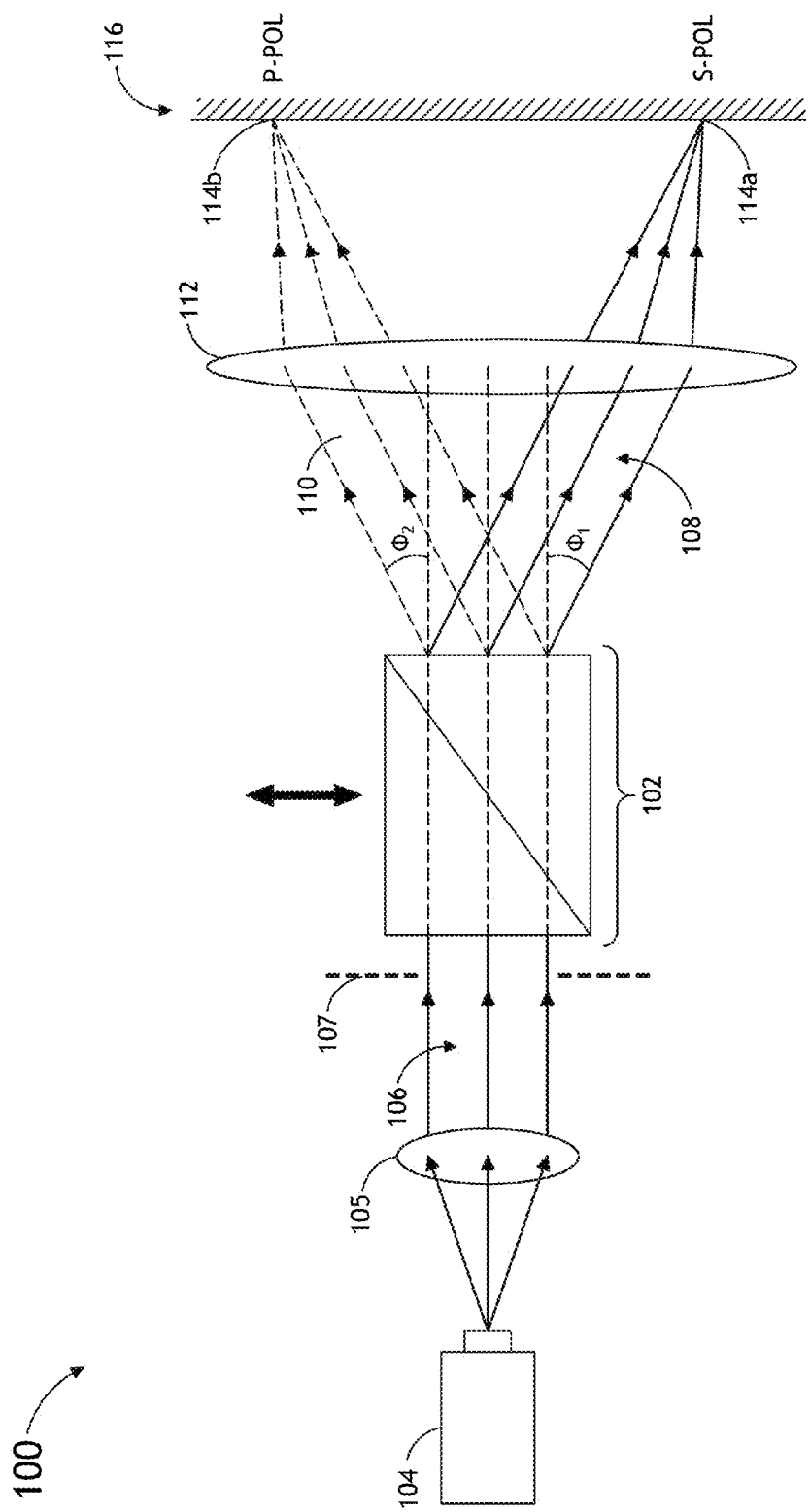
FIG. 1A is a high-level schematic view of an illumination sub-system suitable for generating one or more illumination regions on a substrate, in accordance with one embodiment of the present invention.

FIG. 1A illustrates a simplified schematic view of an illumination sub-system suitable 100 for generating multiple illumination regions on a substrate as a function of polarization, in accordance with one embodiment of the present invention.

In one embodiment, the illumination sub-system 100 includes a polarized illumination deflection element 102, an illumination source 104 and a set of objective optics 112. In one embodiment, the illumination source 104 is configured to generate a primary illumination beam 106. In this regard, light is generated by the illumination source 104 and directed along an illumination pathway defined by a primary illumination direction, as shown in FIG. 1A.

In another embodiment, the polarized illumination deflection element 102 is positioned within the primary beam of illumination 106 or is situated such that the entire primary beam 106 enters the deflection element 102. In another embodiment, the polarized illumination deflection element 102 is positioned at or near the illumination pupil 107 of the illumination sub-system 100. In this regard, the polarized illumination deflection element 102 is configured for deflecting one or more portions of the primary illumination of the primary illumination beam 106 as a function of polarization (e.g., s-polarization or p-polarization) along one or more directions from the primary illumination direction.

In one embodiment, the polarized illumination deflection element 102 is configured to deflect a first portion of the primary illumination beam 106 having a first polarization along a first direction. For example, the polarized illumination deflection element 102 may deflect a portion of the beam having a first polarization along a first direction defined by a first angle $\phi 1$, measured relative to the primary illumination direction, as shown in FIG. 1A.

In another embodiment, the polarized illumination deflection element 102 is configured to deflect a second portion of the primary illumination beam 106 having a second polarization different from the first polarization along a second direction. For example, the polarized illumination deflection element 102 may deflect a portion of the beam having a second polarization along a second direction defined by a second angle $\phi 2$, measured relative to the primary illumination direction, as shown in FIG. 1A. In another embodiment, the second polarization is orthogonal to the first polarization. For instance, the first portion of illumination may include s-polarized light, while the second portion of illumination may include p-polarized light.

It is noted herein that the illumination deflected along the first direction and the second direction may serve to form a first inspection beam 108 and a second illumination beam 110, which are spatially separated from one another and have different polarizations. In another embodiment, the illumination source 104 and polarized illumination deflection element 102 of the illumination sub-system 100 are arranged such that the first inspection beam 108 and the second inspection beam 110 impinge on a substrate 116. In this regard, the first inspection beam 108 and the second inspection beam 110 may form spatially separated illumination spots 114a and 114b respectively.

In another embodiment, the set of objective optics (e.g., one or more objective lenses) 112 are arranged so as to focus the first inspection beam 108 and the second inspection beam 110 onto different regions of the substrate 116. In one embodiment, the set of objective optics 112 may focus the first inspection beam 108 onto a first spot 114a of the substrate 116. In one embodiment, the set of objective optics 112 may focus the second inspection beam 110 onto a second spot 114b of the substrate 116, thereby forming two separated illumination spots 114a and 114b with different polarizations.

In another embodiment, the illumination sub-system 100 includes one or more collimating optical elements 105. For example, the illumination sub-system 100 may include a collimating lens 105 suitable for substantially collimating the primary illumination beam 106 prior to it entering the illumination pupil 107 of the illumination sub-system 100.

Figure 1C:
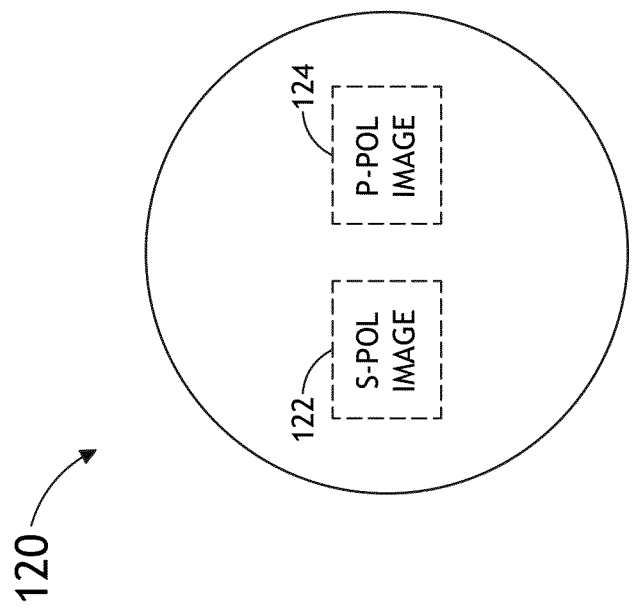
FIG. 1C is a high-level schematic view of a top view of the image plane of an imaging system implementing an illumination sub-system, in accordance with one embodiment of the present invention.
Figure 1B:
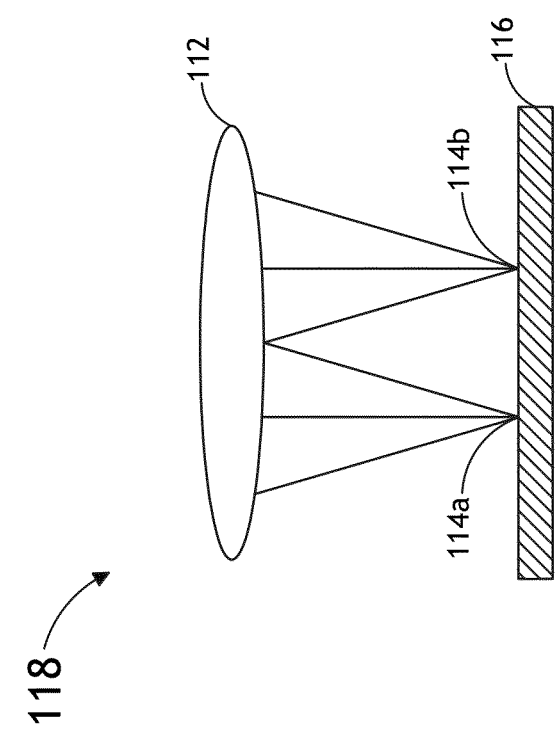
FIG. 1B is a high-level schematic of a side view of a substrate plane, in accordance with one embodiment of the present invention.

FIG. 1B illustrates a side-view 118 of the wafer plane of the illumination sub-system 102, in accordance with one embodiment of the present invention. As shown in FIG. 1B, an objective lens 112 focuses the first inspection beam 108 and the second inspection beam 110 onto different regions of the substrate 116. In one embodiment, the objective lens focuses the first inspection beam 108 onto a first spot 114a of the substrate 116 and the second inspection beam 110 onto a second spot 114b of the substrate 116.

FIG. 1C illustrates a top-view 120 of the image plane of an imaging system implementing the illumination sub-system 100, in accordance with one embodiment of the present invention. As shown in FIG. 1C, an image 122 corresponding with the first spot 114a illuminated with light of a first polarization (e.g., s-polarization) may be imaged onto the image plane of an implementing imaging system, as discussed further herein. Likewise, an image 124 corresponding with the second spot 114b illuminated with light of a second polarization (e.g., p-polarization) may be imaged onto the image plane of an implementing imaging system, also discussed further herein.

The polarized illumination deflection element 102 may include any optical element known in the art capable of selectively deflecting illumination based on polarization of the illumination. In one embodiment, the polarized illumination deflection element 102 includes one or more birefringent optical elements. For example, the polarized illumination deflection element 102 may include a single Wollaston prism (as shown in FIG. 1A), constructed from two individual wedges and including a single optical interface. By way of another example, the polarized illumination deflection element 102 may include a Double Wollaston prism, constructed from three individual wedges and including two optical interfaces. In a general sense, any Wollaston configuration may be utilized with any number of individual wedges and optical interfaces implemented. By way of another example, the polarized illumination deflection element 102 may include a Rochon prism. In a general sense, any Rochon configuration may be utilized with any number of individual wedges and optical interfaces implemented. By way of another example, the polarized illumination deflection element 102 may include a Senarmont prism. In a general sense, any Senarmont prism configuration may be utilized with any number of individual wedges and optical interfaces implemented. It is noted herein that the above birefringent optical elements are not limiting and should be interpreted as merely illustrative of the types of birefringent optical elements that may implement within the context of the present invention.

It is noted herein that the magnitude of the deflections imparted by the deflection element 102 (i.e., size of angle $\phi 1$ or $\phi 2$) may be controlled by controlling one or more physical parameters of the polarized illumination deflection element 102 and/or the utilized illumination. For example, the angles of deflection $\phi 1$, $\phi 2$ may be a function of the component material or materials contained within the polarized illumination deflection element 102. By way of another example, the angles of deflection $\phi 1$, $\phi 2$ may be a function of the orientation of the polarized illumination deflection element 102 with respect to the primary illumination beam 106. By way of another example, the angles of deflection $\phi 1$, $\phi 2$ may be a function of the component prisms (or the number prism interfaces) contained within the polarized illumination deflection element 102. By way of another example, the angles of deflection $\phi 1$, $\phi 2$ may be a function of the spectral makeup (e.g., wavelength components) of the illumination entering the polarized illumination deflection element 102.

It is further noted herein that although FIG. 1A depicts φ1 and φ2 as being non-zero, it is contemplated herein that in some instances either angle φ1 or φ2 may be substantially equal to zero (i.e., parallel with primary illumination direction). For example, light of a first polarization may be deflected at a non-zero angle φ1, while light of a second polarization may be undeflected (i.e., φ2=0) by the polarized illumination deflection element 102. By way of another example, light of a second polarization may be deflected at a non-zero angle φ2, while light of a first polarization may be undeflected (i.e., φ1=0) by the polarized illumination deflection element 102.

The one or more illumination sources 104 may include any illumination source known in the art. For example, the illumination source 104 many include any broadband source known in the art. For instance, the illumination source 104 may include a laser-produced plasma (LPP) source or a discharge-produced plasma (DPP) source. By way of another example, the illumination source 104 may include any narrowband source known in the art. For example, the one or more illumination sources 104 may include one or more lasers. It is further recognized herein that the one or more illumination sources 104 may include multiple individual light sources. For example, in the case of a laser based illumination sub-system, the one or more illumination sources 104 may include multiple individual laser sources. For instance, each individual laser source of a laser based illumination sub-system may emit a different wavelength of light and/or a different polarization state in simultaneously or in a high-frequency sequential pulse train.

Figure 1D:
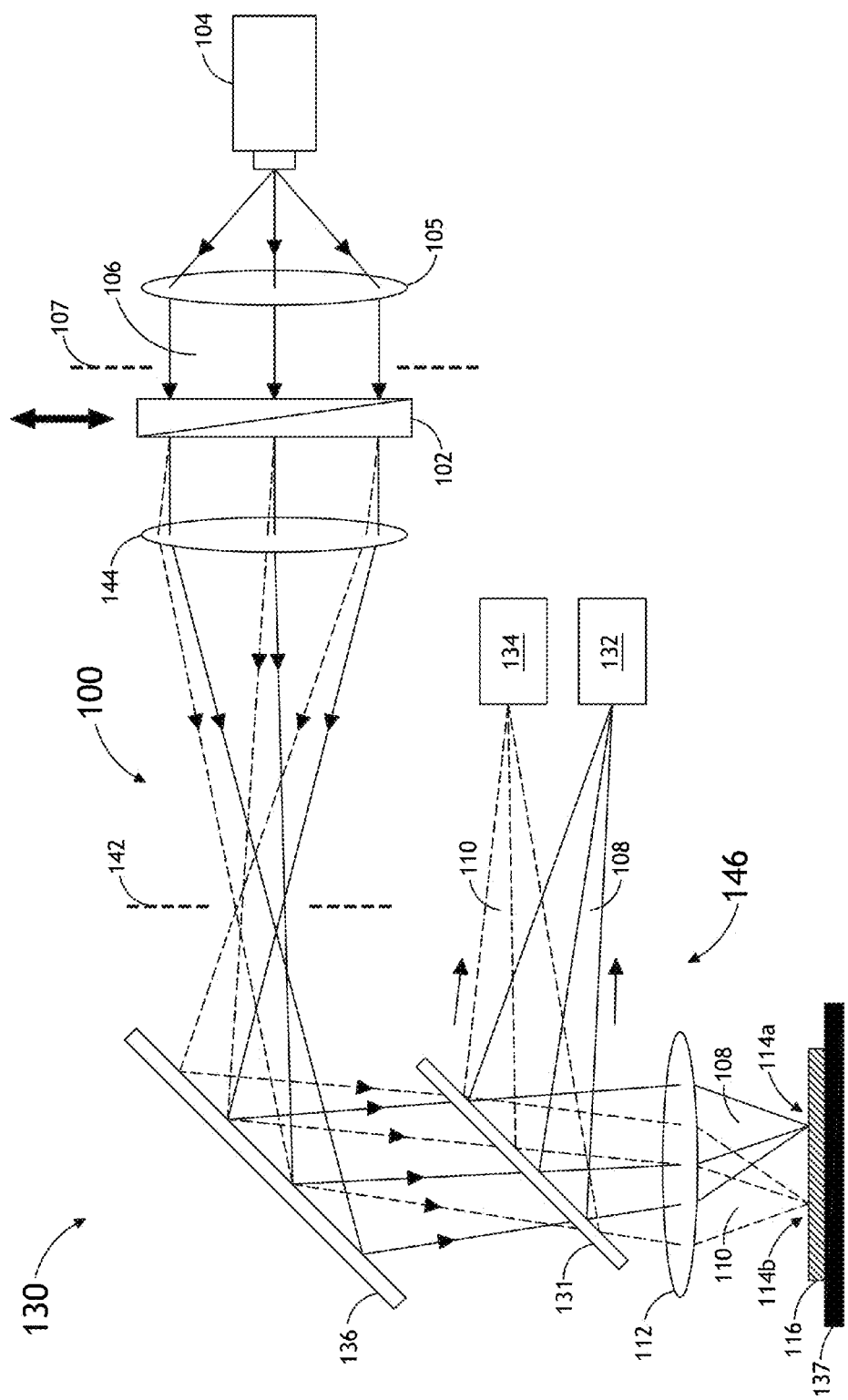
FIG. 1D is a high-level schematic view of an inspection system implementing an illumination sub-system, in accordance with one embodiment of the present invention.

FIG. 1D illustrates an inspection system 130 implementing the illumination sub-system 100, in accordance with one embodiment of the present invention. In one embodiment, the inspection system 130 is configured as a brightfield (BF) inspection system, as shown in FIG. 1D. In another embodiment, the inspection system 130 is configured as a flood illumination inspection system.

As shown in FIG. 1D, the illumination sub-system 100 integrated within the inspection system 130 is arranged to illuminate a substrate (e.g., semiconductor wafer) at two or more separate regions 114a, 114b with light of differing polarization.

In one embodiment, the inspection system 130 includes two or more optical sensors 132 and 134 configured to collect imagery data associated with light from the first inspection beam 108 and the second inspection beam 110, as discussed previously herein. In this regard, the first sensor 132 and the second sensor 134 can be arranged in the image plane of the inspection system 130 such that they separately collect images 122 and 124 (see FIG. 1C) of the first illuminated region 114a and second illuminated region 114b respectively. For instance, image sensor 132 may be arranged so as to image light from the first region 114a, while image sensor 134 may be arranged so as to image light from the second region 114b.

The image sensors 132, 134 may include any image sensors known in the art. For example, one or both of the image sensors 132, 134 may include a CCD sensor. By way of another example, one or both of the image sensors 132, 134 may include a TDI-CCD sensor.

In one embodiment, the inspection system 130 includes one or more beam steering optics 136 (e.g., beam steering mirror) for directing the first inspection beam (solid ray lines) and the second inspection beam (dotted ray lines) emitted from the polarized illumination deflection element 102 toward the surface of the substrate 116 disposed on the substrate stage 137.

In another embodiment, the inspection system 130 includes a set of collection optics for collecting light reflected from the surface of the substrate and directing and focusing the light from each beam 108, 110 onto the image sensors 132 and 134 respectively. In one embodiment, the collection optics of the inspection system 130 includes one or more collection lenses (not shown) positioned within a collection arm 146 of the inspection system 130 and configured to focus light reflected from the first region 114a onto the first image sensor 132 and further configured to focus light reflected from the second region 114b onto the second image sensor 134.

In another embodiment, the inspection system 130 includes a beam splitter 131 arranged within the optical pathway of the inspection system 130. In one embodiment, the beam splitter 131 is configured to allow illumination from the first inspection beam 108 and the second inspection beam 110 emanating from polarized illumination deflection element 102 (and relayed by the beam steering optics 136) to pass through to the substrate 116 (via objective 112). Further, the beam splitter 131 may be configured to direct light reflected from the first region 114a onto the first image sensor 132 and further configured to direct light reflected from the second region 114b onto the second image sensor 134.

In another embodiment, the inspection system 130 includes a focusing lens 144 for focusing light of the first inspection beam 108 and the second inspection beam 110 upon emerging from the polarized illumination deflection element 102. In a further embodiment, the inspection system 130 includes a field stop 142 positioned between the exit surface of the polarized illumination deflection element 102 and the objective 112.

It is noted herein that the inspection system 130 may be arranged in any suitable substrate inspection (e.g., semiconductor wafer inspection) configuration known in the art. Therefore, the optical configuration depicted in FIG. 1D is not limiting and should merely be interpreted as illustrative. For example, the inspection system 130 may be configured to operate without the beam steering optics 131 depicted in FIG. 1D. Further, the beam splitter 131 of the inspection system 130 may be arranged to direct light from the deflection element 102 to the substrate 116, while allowing light reflected from the substrate 116 to pass through to sensors 132 and 134, positioned above the substrate 116 (in contrast to the positioning of sensors 132 and 134 in FIG. 1D). In a general sense, any optical configuration suitable for carrying out reflection mode inspection is suitable for implementation in the context of the present invention.

In another embodiment, the operational state of the polarized illumination deflection element 102 is selectable. For example, the deflection element 102 may be disposed on an actuation stage (not shown) configured to selectably actuate the deflection element 102 into and out of the illumination pathway 106. For instance, the actuation stage may include a linear translation stage, a rotation stage or a combination thereof. In a further embodiment, the actuation stage is communicatively coupled to a controller (not shown) suitable for controlling the actuation state of the deflection element 102. In this regard, the controller may receive instructions from a user (via a user interface) or from a pre-programmed inspection routine and then direct the actuation stage to insert the deflection element 102 into the illumination pathway. Likewise, the controller may receive instructions from a user (via a user interface) or from a pre-programmed inspection routine and then direct the actuation stage to remove the deflection element 102 from the illumination pathway. The insertion and removal of the polarized illumination deflection element 102 is depicted in FIGS. 1A and 1D with an arrow indicative of one example of an actuation direction of the deflection element 102.

In another embodiment, the inspection system 130 may be equipped with a compensation block suitable for compensating the illumination pathway 106 when the polarized deflection element 102 is removed from the pathway 106. For example, upon the removal of the deflection element 102 via a first actuation stage, a second actuation stage (or a second portion of the first actuation stage) may actuate the compensation block into the illumination pathway 106. The compensation block may include any appropriate optical compensating material. For instance, the compensation block may be formed from a glass material of appropriate length for adequate compensation.

Figure 2A:
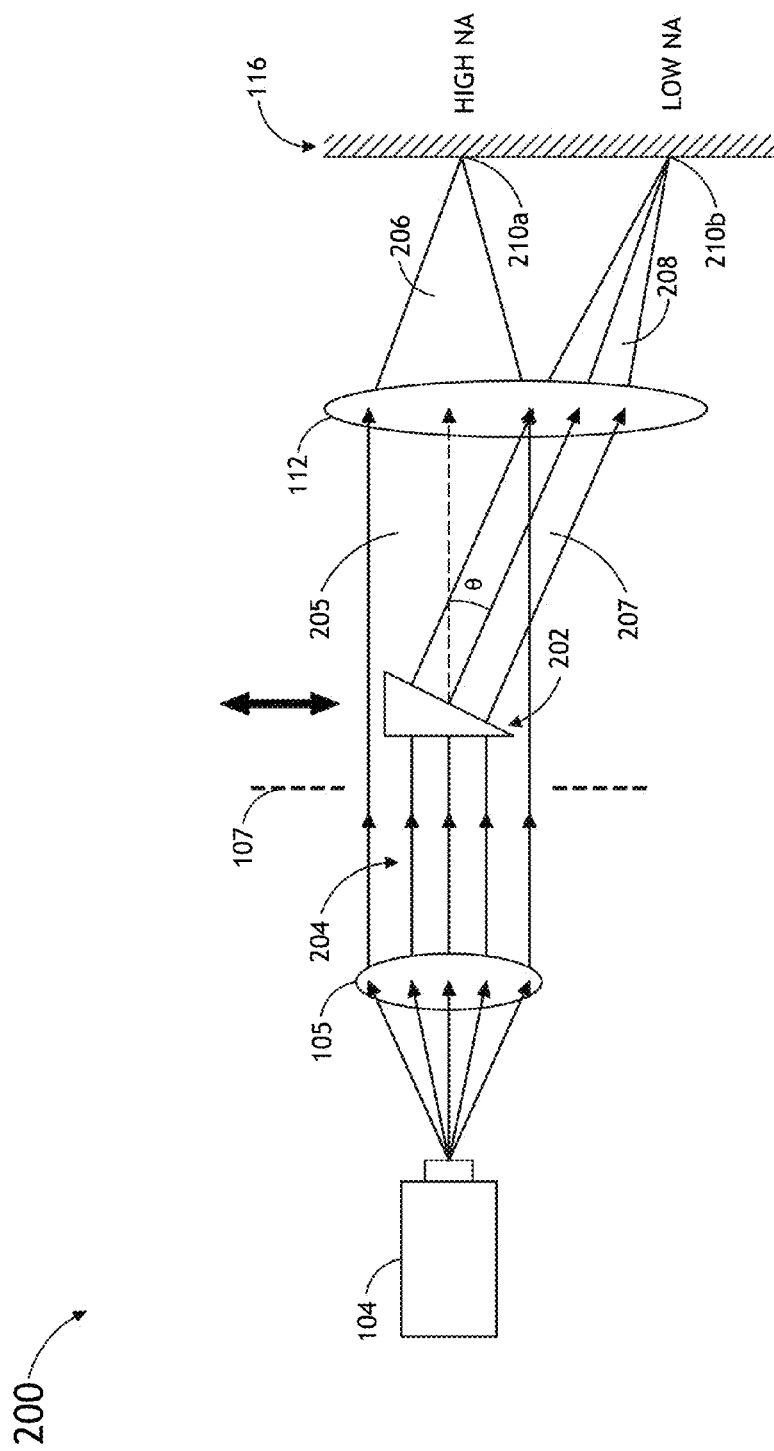
FIG. 2A is a high-level schematic view of an illumination sub-system suitable for generating one or more illumination regions on a substrate, in accordance with one embodiment of the present invention.

Referring now to FIG. 2A, an illumination sub-system for generating multiple illumination regions on a substrate as a function of numerical aperture is illustrated, in accordance with one embodiment of the present invention. The applicant notes that unless otherwise noted the description relating to the illumination sub-system 100 and the inspection system 130 and the components and embodiments thereof (see FIGS. 1A-1D) should be interpreted to extend to the illumination sub-system 200 and inspection system 230 (see FIGS. 2A-2D).

In one embodiment, the illumination sub-system 200 includes one or more angular selection elements 202, an illumination source 104 and a set of objective optics 112. In one embodiment, the illumination source 104 is configured to generate a primary beam of illumination 204. In this regard, light is generated by the illumination source 104 and directed along an illumination pathway defined by a primary illumination direction, as shown in FIG. 2A.

In another embodiment, the angular selection element 202 is positioned within the primary beam of illumination 204. For example, the angular selection element 202 is positioned such that it deflects only a portion of the primary beam of illumination 204 based on the numerical aperture of the light entering the angular selection element 202. In another embodiment, the angular selection element 202 is positioned at or near the illumination pupil 107 of the illumination sub-system 200. In this regard, the angular selection element 202 is configured for deflecting one or more portions of the primary illumination of the primary illumination beam 204 as a function of numerical aperture along one or more directions from the primary illumination direction.

In one embodiment, the angular selection element 202 is situated such that it transmits a portion of the primary beam of illumination having a numerical aperture value above a selected value along a first illumination direction 205 in order to form a first inspection beam 206. In another embodiment, the angular selection element 202 is configured to deflect a portion of the primary beam of illumination having a numerical aperture value below the selected value along a second illumination direction 207 different from the first illumination direction in order to form a second inspection beam 208, as shown in FIG. 2A. For example, the angular selection element 202 may deflect a portion of the beam having a numerical aperture below a selected value along a second direction 207 defined by a deflection angle 8, measured relative to the primary illumination direction, as shown in FIG. 2A.

It is noted herein that the first inspection beam 206 and the second inspection beam 208 are spatially separated from one another and are formed from light with differing numerical aperture. In another embodiment, the illumination source 104 and the angular selection element 202 of the illumination sub-system 200 are arranged such that the first inspection beam 206 and the second inspection beam 208 impinge on a substrate 116. In this regard, the first inspection beam 206 and the second inspection beam 208 may form spatially separated illumination spots 210a and 210b respectively.

In another embodiment, the set of objective optics (e.g., one or more objective lenses) 112 are arranged so as to focus the first inspection beam 206 and the second inspection beam 208 onto different regions of the substrate 116. In one embodiment, the set of objective optics 112 may focus the first inspection beam 206 onto a first spot 210a of the substrate 116. In one embodiment, the set of objective optics 112 may focus the second inspection beam 208 onto a second spot 210b of the substrate 116, thereby forming two separated illumination spots 210a and 210b formed with light of differing numerical aperture.

FIG. 2B illustrates a side-view 212 of the wafer plane of the illumination sub-system 202, in accordance with one embodiment of the present invention. As shown in FIG. 1B, the objective lens 112 focuses the first inspection beam 206 and the second inspection beam 208 onto different regions of the substrate 116. In one embodiment, the objective lens focuses the first inspection beam 206 onto a first spot 210a of the substrate 116, while focusing the second inspection beam 208 onto a second spot 210b of the substrate 116.

FIG. 2C illustrates a top-view 220 of the image plane of an imaging system implementing the illumination sub-system 200, in accordance with one embodiment of the present invention. As shown in FIG. 2C, an image 214 corresponding with the first spot 210a illuminated with light having a numerical aperture above a selected value (i.e., "high-NA") may be imaged onto the image plane of an implementing imaging system, as discussed further herein. Likewise, an image 216 corresponding with the second spot 210b illuminated with light having a numerical aperture below a selected numerical aperture (i.e., "low-NA") may be imaged onto the image plane of an implementing imaging system, also discussed further herein.

Figure 2D:
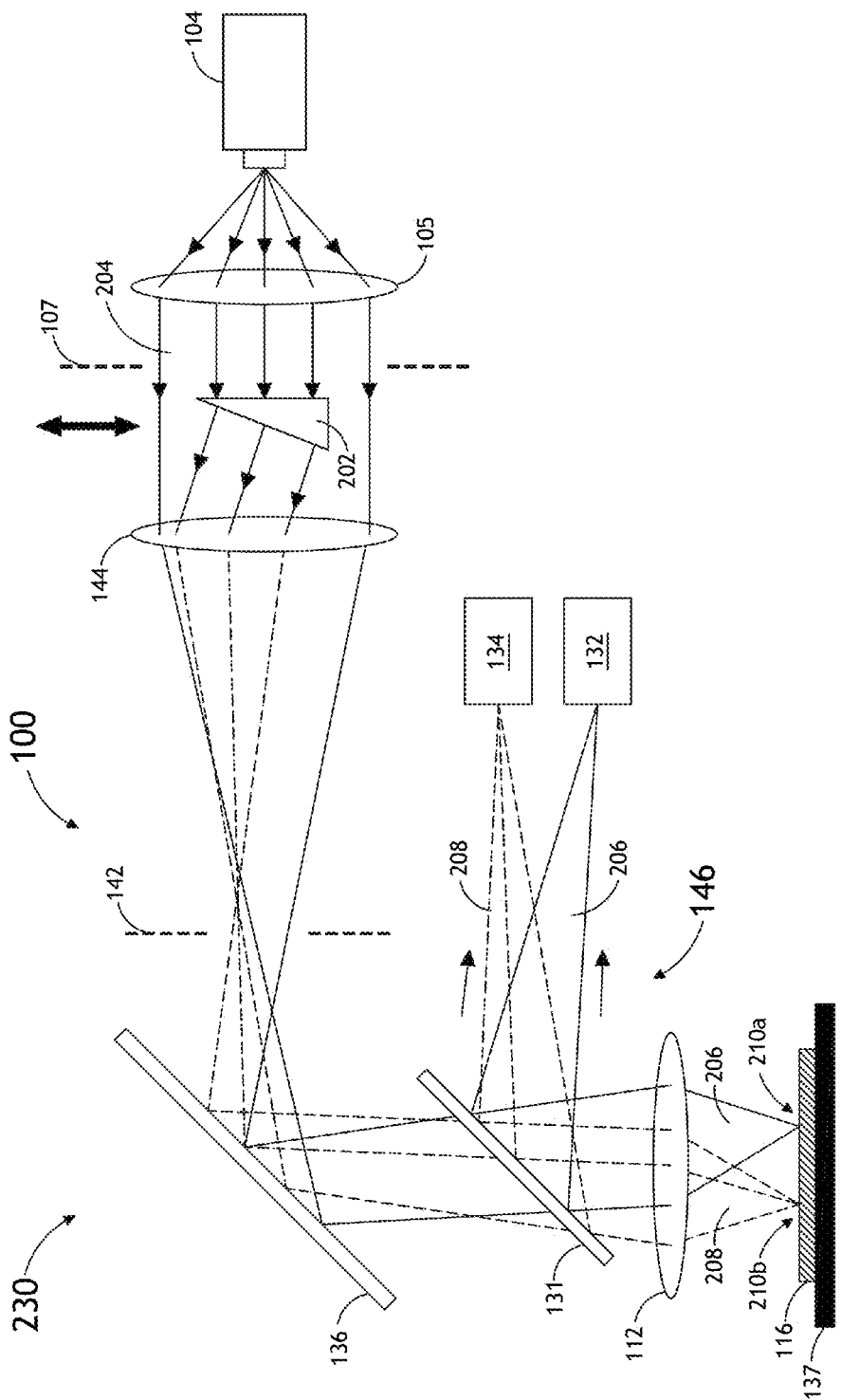
FIG. 2D is a high-level schematic view of an inspection system implementing an illumination sub-system, in accordance with one embodiment of the present invention.

The angular deflection element 202 may include any optical element known in the art capable of selectively deflecting illumination of the illumination beam 204 based on the numerical aperture of one or more portions of the beam. In one embodiment, the angular selection element includes one or more optical wedge plates, as shown in FIGS. 2A and 2D. For example, as shown in FIGS. 2A and 2D, the angular selection element 202 may include a single wedged plate. By way of another example, although not shown, the angular selection element 202 may include multiple wedged plates.

It is noted herein that the magnitude of deflection as well as the level of numerical aperture of light for deflection may be controlled by controlling one or more physical parameters of the angular selection element 202. For example, the angle of deflection of θ of light having a numerical aperture below a selected value may be controlled by the angle of the exit face of the angular selection element 202. Further, the value of the numerical aperture of light that is deflected via the angular selection element 202 can be controlled by controlling the size of the entry face of the angular selection element 202, as shown in FIG. 1A.

FIG. 2D illustrates an inspection system 230 implementing the illumination sub-system 200, in accordance with one embodiment of the present invention. In one embodiment, the inspection system 230 is configured as a brightfield (BF) inspection system, as shown in FIG. 2D. In a further embodiment, the inspection system 230 is configured as a flood illumination inspection system.

As shown in FIG. 2D, the illumination sub-system 200 integrated within the inspection system 230 is arranged to illuminate the substrate 116 at two or more spatially separated regions 210a, 210b with light of differing numerical aperture.

In one embodiment, the two or more optical sensors 132 and 134 of the inspection system 230 are configured to collect imagery data associated with light from the first inspection beam 206 and the second inspection beam 208, as discussed previously herein. In this regard, the first sensor 132 and the second sensor 134 can be arranged in the image plane of the inspection system 230 such that they separately collect images 214 and 216 (see FIG. 2C) of the first illuminated region 210a and the second illuminated region 210b respectively. For instance, image sensor 132 may be arranged so as to image light from the first region 210a, while image sensor 134 may be arranged so as to image light from the second region 210b.

In one embodiment, the inspection system 230 includes one or more beam steering optics 136 (e.g., beam steering mirror) for directing the first inspection beam (solid ray lines) and the second inspection beam (dotted ray lines) emitted from the angular deflection element 202 toward the surface of the substrate 116 disposed on the substrate stage 137.

In another embodiment, the inspection system 230 includes a set of collection optics for collecting light reflected from the surface of the substrate 116 and directing and focusing the light from each beam 206, 208 onto the image sensors 132 and 134 respectively. In one embodiment, the collection optics of the inspection system 230 include one or more collection lenses (not shown) positioned within a collection arm 146 of the inspection system 230 and configured to focus light reflected from the first region 210a onto the first image sensor 132 and further configured to focus light reflected from the second region 210b onto the second image sensor 134.

In another embodiment, the inspection system 230 includes a beam splitter 131 arranged within the optical pathway of the inspection system 230. In one embodiment, the beam splitter 131 is configured to allow illumination from the first inspection beam 206 and the second inspection beam 208 emanating from angular selection element 202 (and relayed by the beam steering optics 136) to pass through to the substrate 116 (via objective 112). Further, the beam splitter 131 may be configured to direct light reflected from the first region 210a onto the first image sensor 132 and further configured to direct light reflected from the second region 210b onto the second image sensor 134.

In another embodiment, the inspection system 230 includes a focusing lens 144 for focusing light of the first inspection beam 206 and the second inspection beam 208 upon emerging from the angular selection element 202. In a further embodiment, the inspection system 230 includes a field stop 142 positioned between the exit surface of the angular selection element 202 and the objective 112.

It is noted herein that the inspection system 230 may be arranged in any suitable substrate inspection (e.g., semiconductor wafer inspection) configuration known in the art. Therefore, the optical configuration depicted in FIG. 2D is not limiting and should merely be interpreted as illustrative. For example, the inspection system 230 may be configured to operate without the beam steering optics 131 depicted in FIG. 2D. Further, the beam splitter 131 of the inspection system 230 may be arranged to direct light from the angular selection element 202 to the substrate 116, while allowing light reflected from the substrate 116 to pass through to sensors 132 and 134, positioned above the substrate 116 (in contrast to the positioning of sensors 132 and 134 in FIG. 2D). In a general sense, any optical configuration suitable for carrying out inspection is suitable for implementation in the context of the present invention.

In another embodiment, the operational state of the angular selection element 202 is selectable. For example, the angular selection element 202 may be disposed on an actuation stage (not shown) configured to selectably actuate the angular selection element 202 into and out of the illumination pathway 204. For instance, the actuation stage may include a linear translation stage, a rotation stage or a combination thereof. In a further embodiment, the actuation stage is communicatively coupled to a controller (not shown) suitable for controlling the actuation state of the angular selection element 202. In this regard, the controller may receive instructions from a user (via a user interface) or from a pre-programmed inspection routine and then direct the actuation stage to insert the angular selection element 202 into the illumination pathway. Likewise, the controller may receive instructions from a user (via a user interface) or from a pre-programmed inspection routine and then direct the actuation stage to remove the angular selection element 202 from the illumination pathway. The insertion and removal of the angular selection element 202 is depicted in FIGS. 2A and 2D with an arrow, which indicates one example of an actuation direction of the angular selection element 202.

In another embodiment, the inspection system 230 may be equipped with a compensation block suitable for compensating the illumination pathway 204 when the angular selection element 202 is removed from the pathway 204. For example, upon the removal of the angular selection element 202 via a first actuation stage, a second actuation stage (or a second portion of the first actuation stage) may actuate the compensation block into the illumination pathway 204. The compensation block may include any appropriate optical compensating material. For instance, the compensation block may be formed from a glass material of appropriate length for adequate compensation.

While the present invention has focused on using the angular selection element 202 based on numerical aperture values in order to image two or more spatially separated regions 210a, 210b, it is further contemplated herein that the present invention may be extended to an angular selection element 202 configured to direct light from any portion of the illumination pupil 107 to a spatially separate region of the substrate 116. In one embodiment of FIG. 2D (although not shown), the physical parameters of angular deflection element 202 are selectable. For example, the size and the position of the angular deflection element in subsystem 230 may be controlled. In one instance, the angular deflection element 202 may be positioned near the collimating lens 105 and the illumination pupil 107. Further, a portion of the primary illumination beam 204 from the illumination pupil 107 may be collected by controlling the size of the angular deflection element 202. Any number of the inspection system collection optics, (e.g. focusing lens 144, the beam steering optics 136, beam splitter 131) may be used to transmit the primary illumination beam 204 after a portion has passed through the angular deflection element 202 to the objective 112, which focuses the illumination beam 204 onto the substrate 116. In this regard, a portion of the primary illumination beam 204 may be projected onto any spatially separated region on the substrate 116.

Referring now to FIGS. 3A through 3D, the placement of an aperture 334 in a collection pupil 332 is illustrated, in accordance with one embodiment of the present invention. The applicant notes that unless otherwise noted the description relating to the illumination sub-systems 100 and 200, the inspection systems 130 and 230, and the components and embodiments thereof (see FIGS. 1A-1D and 2A-2D) should be interpreted to extend to FIGS. 3A-3D.

FIG. 3A illustrates a top view 300 of the illumination pupil 107. In one embodiment, the angular deflection element 202 is positioned at or near the illumination pupil 107. Further, the illumination pupil 107 has a minimum numerical aperture value 304 and a maximum numerical aperture value 306. In another embodiment, the physical parameters of the angular deflection element 202 are configured such that a portion of the primary beam of illumination 104 remains undeflected and is transmitted through the open area 302 of the illumination pupil 107.

FIG. 3B illustrates a top view 310 of a collection pupil. In one embodiment, the angular deflection element 202 is positioned at or near the illumination pupil 107. Further, the illumination pupil 107 has a minimum numerical aperture value 304 and a maximum numerical aperture value 306. In another embodiment, the illumination pupil 107 aperture value range is correlated to the size and position of the angular deflection element 202.

FIG. 3C illustrates a top view 320 of an image plane with a field radius 322 of an imaging system implementing the illumination sub-system 200, in accordance with one embodiment of the present invention. As shown in FIG. 3C, a brightfield (BF) image 324 is illuminated with light having a numerical aperture value outside of the range blocked by the aperture 334. Further, a darkfield (DF) image 326 is illuminated on the image plane. In one embodiment, the darkfield image 326 is formed if the numerical aperture range blocked by the aperture 334 is conjugate to the range of numerical aperture values of the light undeflected by the angular deflection element 202 passing through the illumination pupil 107.

In another embodiment, the aperture 334 is positioned within the inspection beams 206, 208 or is situated such that the entirety of either inspection beam 206, 208 enters the aperture 334. In another embodiment, the aperture 334 is positioned at or near the collection pupil 332 of the inspection system 330. In another embodiment, the aperture 334 is positioned such that a portion of inspection beam 206, inspection beam 208, or both passes through the aperture 334. In this regard, the aperture 334 is configured for blocking one or more portions of the inspection beams 206, 208.

The aperture 334 may include any optical element known in the art capable of selectively blocking illumination of one or more of the illumination beam 204 or inspection beams 206, 208 based on the numerical aperture of one or more portions of the beam. In one embodiment, the aperture 334 includes an adjustable system of one or more blades configured to move coincidentally (e.g. shutter) to create one or more numerical aperture values. In one embodiment, the aperture 334 may be manually manipulated by the user to increase the numerical aperture value. Likewise, the aperture 334 may be manually manipulated by the user to decrease the numerical aperture value. It another embodiment, the numerical aperture value is changed by means of a controller. For instance, the controller may receive instructions from a user (via a user interface) or from a pre-programmed inspection routine and then direct the aperture 334 to adjust the adjustment mechanism and increase the numerical aperture value. Likewise, the controller may receive instructions from a user (via a user interface) or from a pre-programmed inspection routine and then direct the aperture 334 to adjust the adjustment mechanism and decrease the numerical aperture value.

Figure 3D:
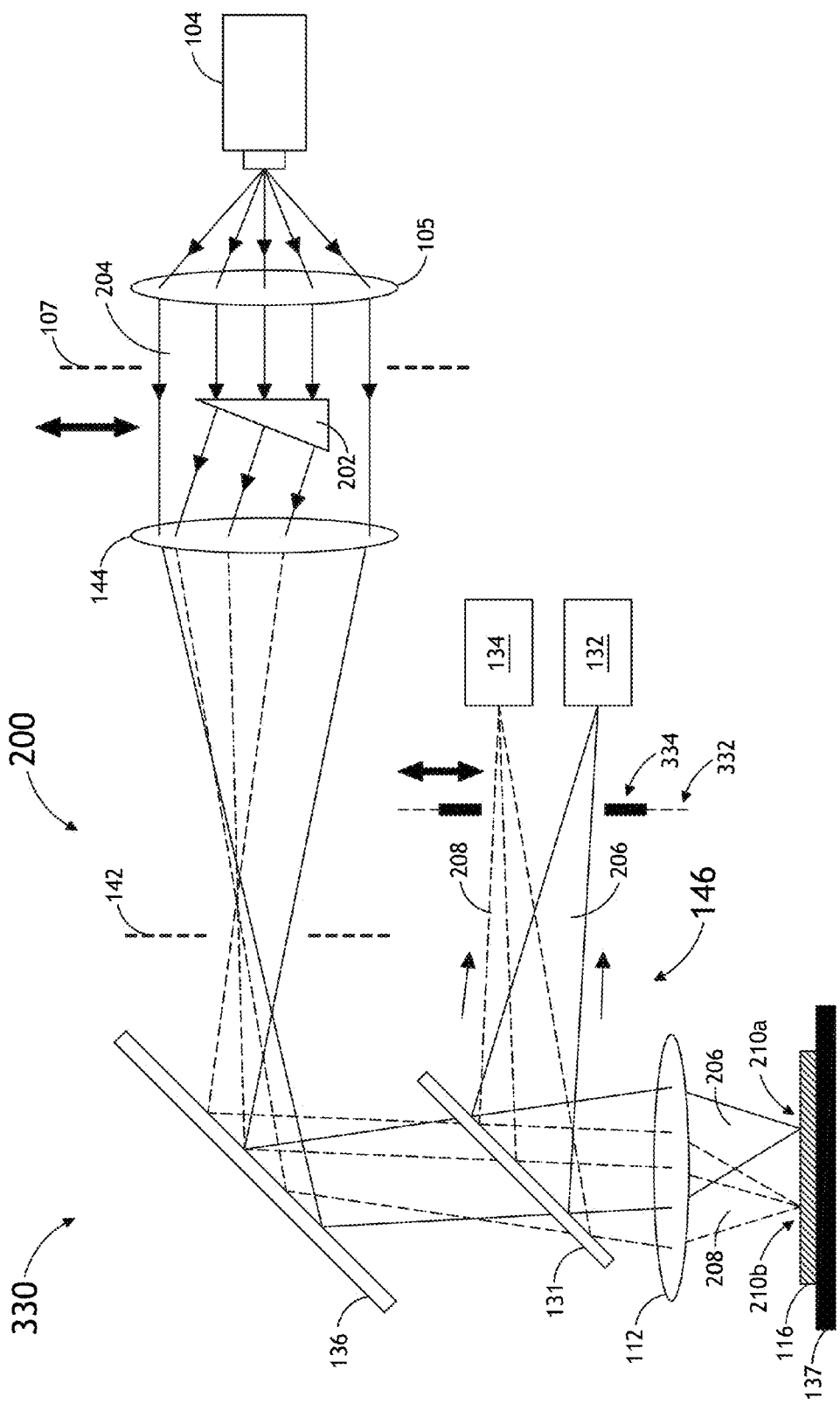
FIG. 3D is a high-level schematic view of an inspection system implementing an illumination sub-system, in accordance with one embodiment of the present invention.

In another embodiment, the numerical aperture value of aperture 334 is fixed and the aperture 334 is fully removable from the inspection system 330 shown in FIG. 3D. For instance, the aperture 334 may be manually removed by the user. By way of another example, the aperture 334 may be disposed on an actuation stage (not shown) configured to selectably actuate the aperture 334 into and out either or both of the pathways for inspection beams 206 and 208. For instance, the actuation stage may include a linear translation stage, a rotation stage or a combination thereof. In a further embodiment, the actuation stage is communicatively coupled to a controller (not shown) suitable for controlling the actuation state of the aperture 334. In this regard, the controller may receive instructions from a user (via a user interface) or from a pre-programmed inspection routine and then direct the actuation stage to insert the aperture 334 into the illumination pathway. Likewise, the controller may receive instructions from a user (via a user interface) or from a pre-programmed inspection routine and then direct the actuation stage to remove the aperture 334 from the inspections beams pathways. The insertion and removal of the aperture 334 is depicted in FIG. 3D with an arrow indicative of one example of an actuation direction of the aperture 334. Further, the fixed numerical aperture value aperture 334 may be part of a set of at least two interchangeable components.

FIG. 3D illustrates an inspection system 330 implementing the illumination sub-system 200, in accordance with one embodiment of the present invention. In one embodiment, the inspection system 330 is configured as a brightfield inspection system. In another embodiment, the angular selection element 202 is positioned such that it deflects some portion of the primary beam of illumination 204 based on the numerical aperture of the light entering the angular selection element 202. In another embodiment, the system of optical devices previously discussed herein transmits a portion of the primary beam of illumination 204 to create inspection beams 206, 208, which are focused on spatially separated regions 210a, 210b. In this regard, the illumination sub-system 200 integrated within the inspection system 330 is arranged to illuminate the substrate 116 at two or more spatially separated regions 210a, 210b with light of differing numerical aperture.

In one embodiment, the two or more optical sensors 132 and 134 of the inspection system 330 are configured to collect imagery data associated with light from the first inspection beam 206 and the second inspection beam 208, as discussed previously herein. In another embodiment, the inspection system 330 includes one or more aperture 334 in a portion of one or more of the inspection beams 206, 208. Further, the aperture 334 is configured to block a chosen range of numerical aperture values. In this regard, the blocked numerical aperture values create a darkfield image 326 of the transmitted illuminations of substrate 116.

The first sensor 132 and the second sensor 134 can be arranged in the image plane of the inspection system 330 such that they separately collect the brightfield image 324 and the darkfield image 326 (see FIG. 3C). For instance, image sensor 132 may be arranged so as to image light from the brightfield image 324. Likewise, image sensor 134 may be arranged so as to image light from the darkfield image 326.

The embodiments of systems 100 and 130 illustrated in FIGS. 1A-1D may be further configured as described herein. In addition, the illumination sub-system 100 and the inspection system 130 may be configured to perform any other step(s) of any of the method embodiment(s) described herein.

Figure 4:
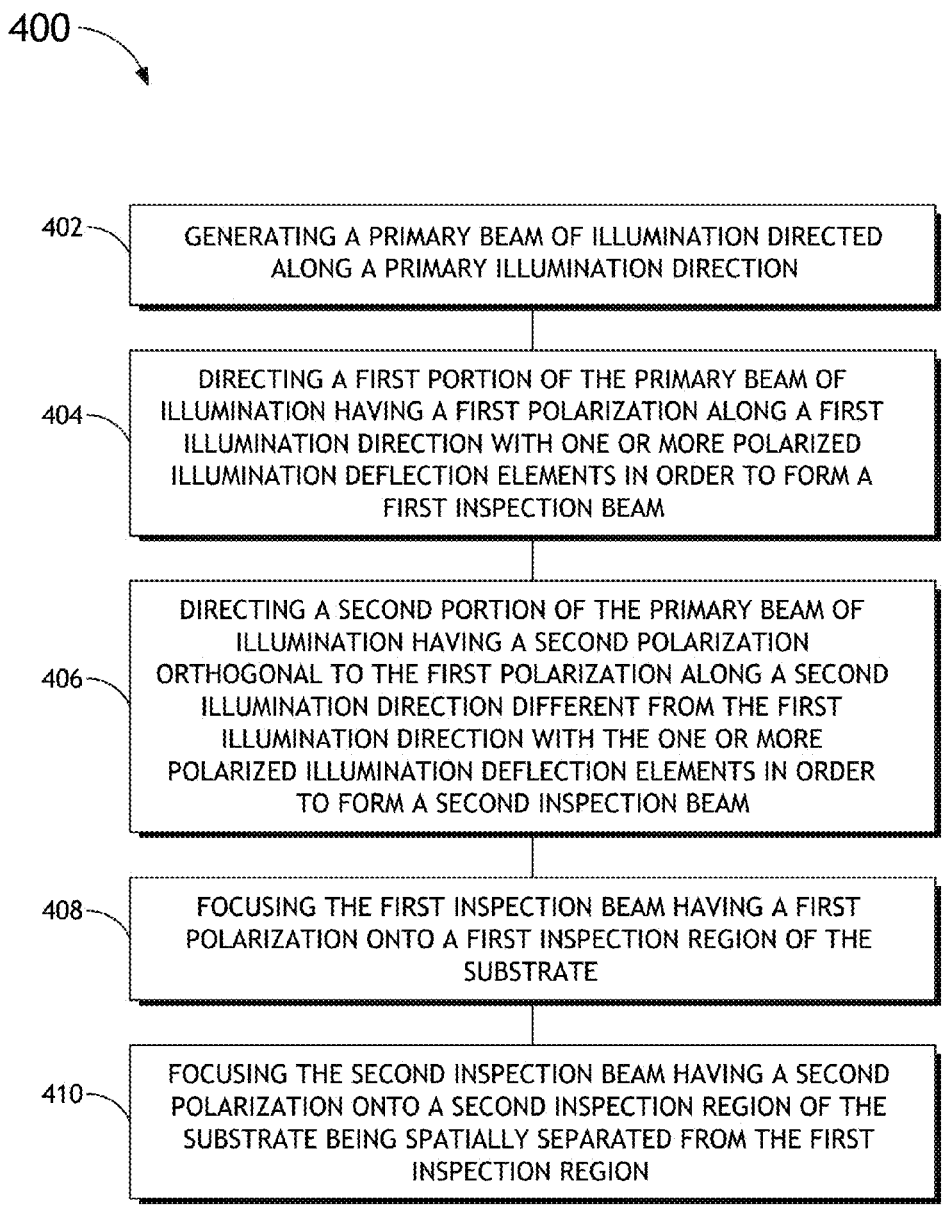
FIG. 4 is a process flow diagram illustrating a method for generating two or more spatially separated inspection regions on a substrate, in accordance with one embodiment of the present invention.

FIG. 4 illustrates a process flow 400 suitable for generating two or more spatially separated inspection regions on a substrate. In step 402, a primary beam of illumination directed along a primary illumination direction is generated. In step 404, a first portion of the primary beam of illumination having a first polarization is directed along a first illumination direction with one or more polarized illumination deflection elements in order to form a first inspection beam. In step 406, a second portion of the primary beam of illumination having a second polarization orthogonal to the first polarization is directed along a second illumination direction different from the first illumination direction with the one or more polarized illumination deflection elements in order to form a second inspection beam. In step 408, the first inspection beam having a first polarization is focused onto a first inspection region of the substrate. In step 410, the second inspection beam having a second polarization is focused onto a second inspection region of the substrate being spatially separated from the first inspection region. In a further step, the image from the first inspection region is imaged onto a first sensor and the second inspection region is imaged onto a second sensor, the first sensor and second sensor disposed at a common image plane.

The embodiments of systems 200 and 230 illustrated in FIGS. 2A-2D may be further configured as described herein. In addition, the illumination sub-system 200 and the inspection system 230 may be configured to perform any other step(s) of any of the method embodiment(s) described herein.

Figure 5:
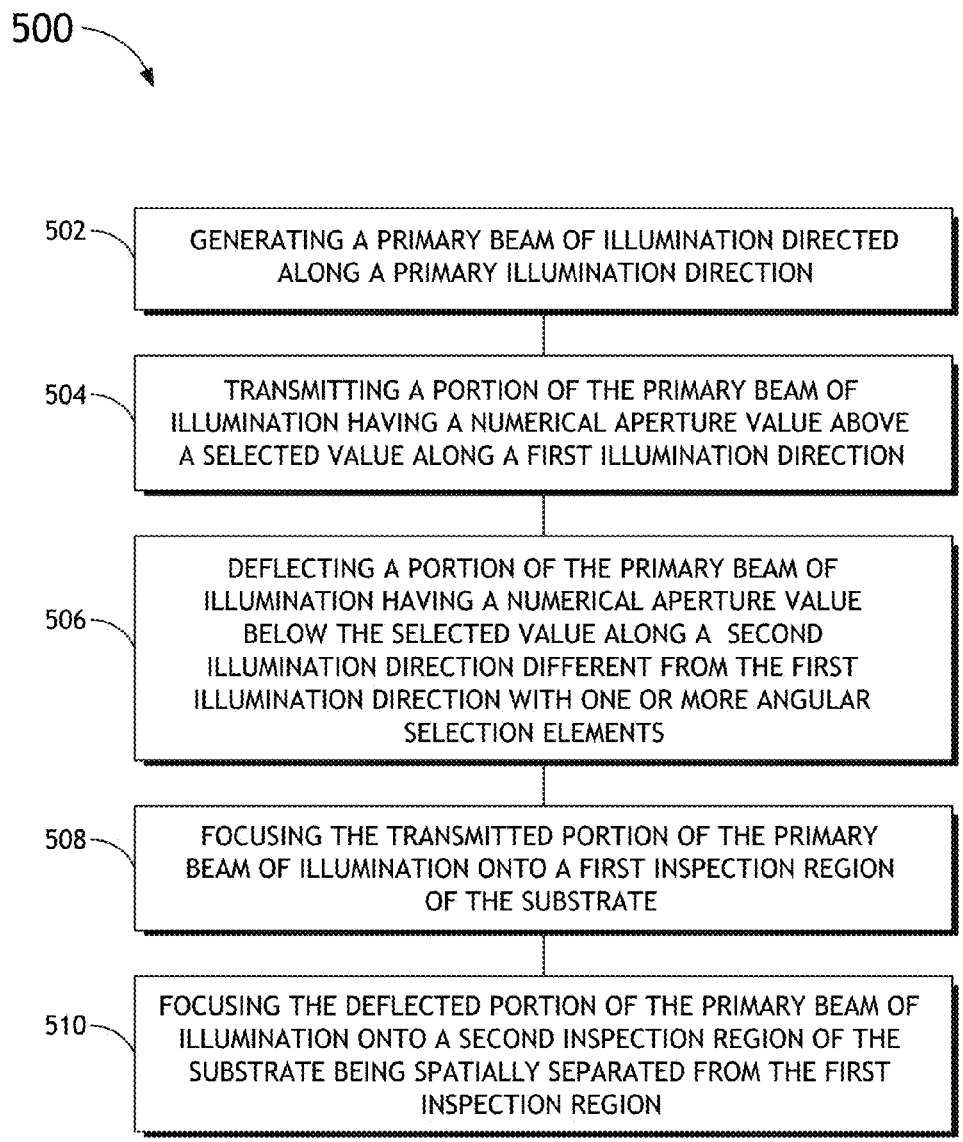
FIG. 5 is a process flow diagram illustrating a method for generating two or more spatially separated inspections regions on a substrate, in accordance with one embodiment of the present invention.

FIG. 5 illustrates a process flow 500 suitable for generating two or more spatially separated inspection regions on a substrate. In step 502, a primary beam of illumination directed along a primary illumination direction is generated. In step 504, a portion of the primary beam of illumination having a numerical aperture value above a selected value is transmitted along a first illumination direction. In step 506, a portion of the primary beam of illumination having a numerical aperture value below the selected value is deflected along a second illumination direction different from the first illumination direction with one or more angular selection elements. In step 508, the transmitted portion of the primary beam of illumination is focused onto a first inspection region of the substrate. In step 510, the deflected portion of the primary beam of illumination is focused onto a second inspection region of the substrate being spatially separated from the first inspection region. In a further step, the image from the first inspection region is imaged onto a first sensor and the second inspection region is imaged onto a second sensor, the first sensor and second sensor disposed at a common image plane.

Figure 6:
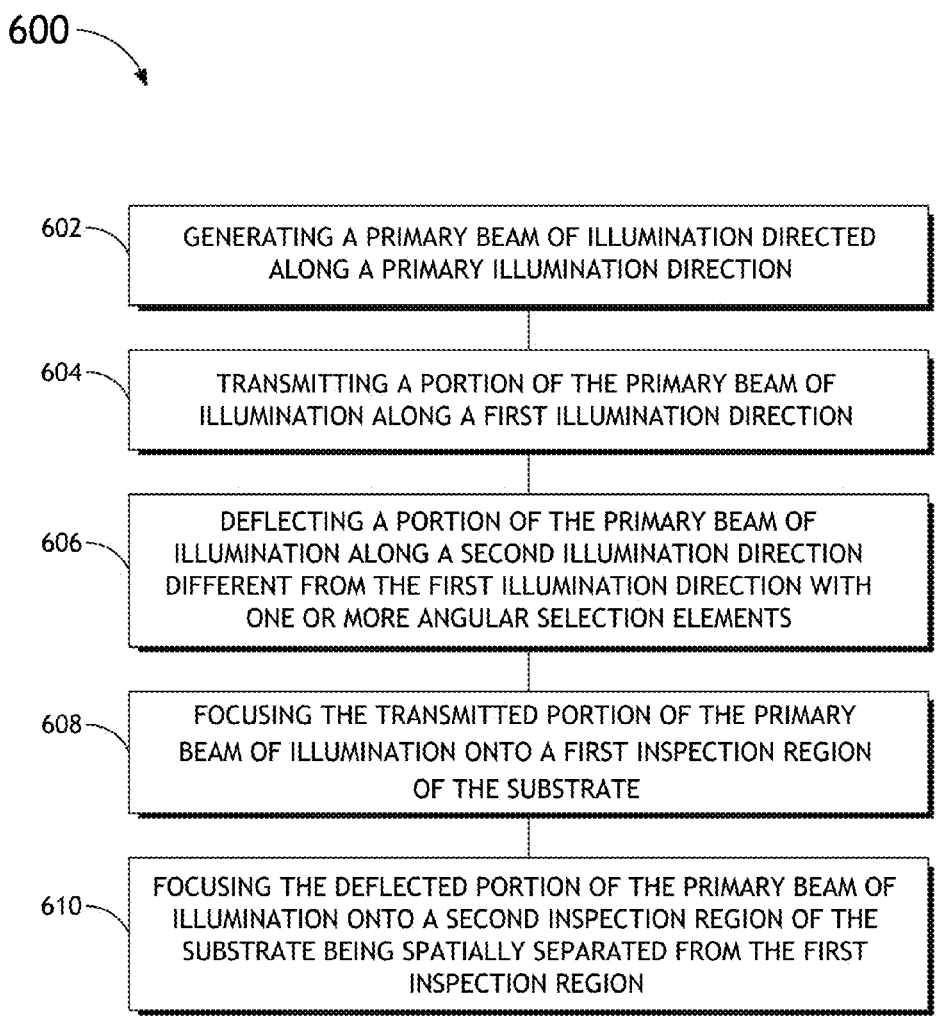
FIG. 6 is a process flow diagram illustrating a method for generating two or more spatially separated inspections regions on a substrate, in accordance with one embodiment of the present invention.

FIG. 6 illustrates a process flow 600 suitable for generating two or more spatially separated inspection regions on a substrate. In step 602, a primary beam of illumination directed along a primary illumination direction is generated. In step 604, a portion of the primary beam of illumination is transmitted along a first illumination direction. In step 606, a portion of the primary beam of illumination is deflected along a second illumination direction different from the first illumination direction with one or more angular selection elements. In step 608, the transmitted portion of the primary beam of illumination is focused onto a first inspection region of the substrate. In step 610, the deflected portion of the primary beam of illumination is focused onto a second inspection region of the substrate being spatially separated from the first inspection region. In a further step, the image from the first inspection region is imaged onto a first sensor and the second inspection region is imaged onto a second sensor, the first sensor and second sensor disposed at a common image plane.

The embodiments of inspection system 330 illustrated in FIG. 3D may be further configured as described herein. In addition, the inspection system 330 may be configured to perform any other step(s) of any of the method embodiment(s) described herein.

Figure 7:
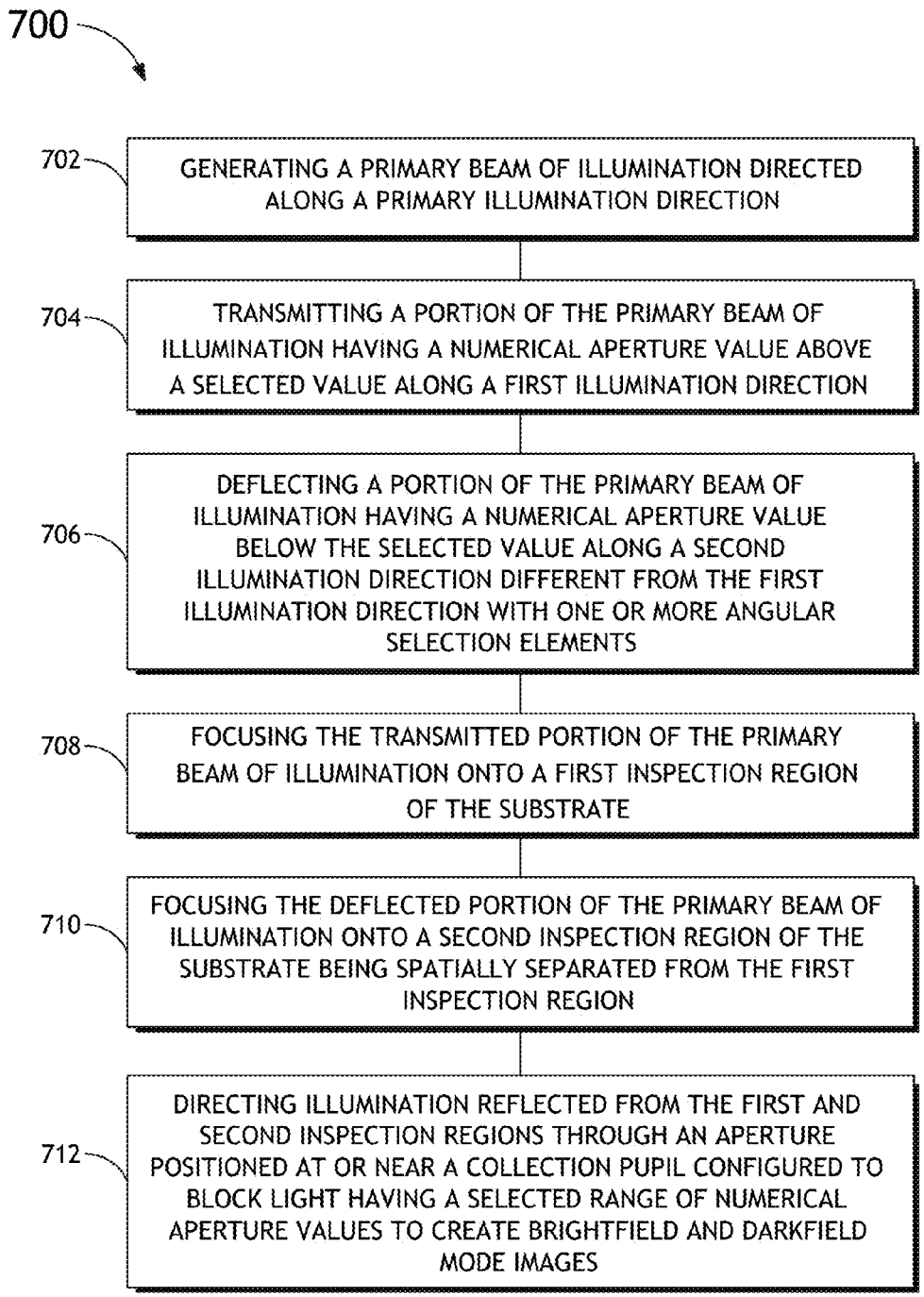
FIG. 7 is a process flow diagram illustrating a method for generating two or more spatially separated inspections regions on a substrate, in accordance with one embodiment of the present invention.

FIG. 7 illustrates a process flow 700 suitable for generating two or more spatially separated inspection regions on a substrate. In step 702, a primary beam of illumination directed along a primary illumination direction is generated. In step 704, a portion of the primary beam of illumination having a numerical aperture value above a selected value is transmitted along a first illumination direction. In step 706, a portion of the primary beam of illumination having a numerical aperture value below the selected value is deflected along a second illumination direction different from the first illumination direction with one or more angular selection elements. In step 708, the transmitted portion of the primary beam of illumination is focused onto a first inspection region of the substrate. In step 710, the deflected portion of the primary beam of illumination is focused onto a second inspection region of the substrate being spatially separated from the first inspection region. In step 712, light from the inspection regions is directed through an aperture positioned at or near a collection pupil configured to block light having a selected range of numerical aperture values to create brightfield and darkfield mode images. In a further step, the image from the first inspection region is imaged onto a first sensor and the second inspection region is imaged onto a second sensor, the first sensor and second sensor disposed at a common image plane.

All of the system and methods described herein may include storing results of one or more steps of the method embodiments in a storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. Furthermore, the results may be stored "permanently," "semi-permanently," temporarily, or for some period of time. For example, the storage medium may be random access memory (RAM), and the results may not necessarily persist indefinitely in the storage medium.

Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "connected", or "coupled", to each other to achieve the desired functionality, and any two components capable of being so associated can also be viewed as being "couplable", to each other to achieve the desired functionality. Specific examples of couplable include but are not limited to physically mateable and/or physically interacting components and/or wirelessly interactable and/or wirelessly interacting components and/or logically interactable and/or logically interacting components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein.

Although particular embodiments of this invention have been illustrated, it is apparent that various modifications and embodiments of the invention may be made by those skilled in the art without departing from the scope and spirit of the foregoing disclosure. Accordingly, the scope of the invention should be limited only by the claims appended hereto.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

Furthermore, it is to be understood that the invention is defined by the appended claims.

What is claimed is:

1. An inspection system comprising:
    an illumination source for generating a primary beam of illumination directed along a primary illumination direction;
    one or more actuatable polarized illumination deflection elements selectively actuatable into the primary beam of illumination, the one or more actuatable illumination deflection elements configured to direct a first portion of the primary beam of illumination having a first polarization along a first illumination direction in order to form a first inspection beam, the one or more actuatable illumination deflection elements further configured to direct a second portion of the primary beam having a second polarization orthogonal to the first polarization along a second illumination direction in order to form a second inspection beam, the second illumination direction different from the first illumination direction; and
    an objective configured to focus the first inspection beam having the first polarization onto a first region of a substrate, the objective further configured to focus the second inspection beam having the second polarization onto a second region of the substrate, the first region being spatially separated from the second region; and
    one or more image sensors, wherein the one or more image sensors are configured so as to separately collect illumination emanating from the first region of the substrate and illumination emanating from the second region of the substrate, wherein the illumination emanating from the first region of the substrate is non-interfering with the illumination emanating from the second region of the substrate.

2. The illumination apparatus of claim 1, wherein at least one of the first polarization or the second polarization comprises:
    at least one of s-polarization and p-polarization.

3. The illumination apparatus of claim 1, wherein the one or more actuatable polarized illumination deflection elements comprise:
    one or more birefringent optical elements.

4. The illumination apparatus of claim 3, wherein the one or more birefringent optical elements comprise:
    at least one of a Single Wollaston prism, a Double Wollaston prism, a Rochon Prism or a Senarmont Prism.

5. The illumination apparatus of claim 1, wherein the one or more actuatable illumination deflection elements are configured to transmit a portion of the primary beam of illumination having a first polarization along a first illumination direction in order to form the first inspection beam, the first illumination direction being substantially collinear to the primary beam direction.

6. The illumination apparatus of claim 1, wherein the one or more actuatable illumination deflection elements are configured to deflect a portion of the primary beam of illumination having a first polarization along a first illumination direction in order to form the first inspection beam, the first illumination direction different from the primary illumination direction.

7. The illumination apparatus of claim 1, wherein the one or more illumination sources comprise:
at least one of one or more broadband sources or one or more narrowband sources.

8. The illumination apparatus of claim 1, further comprising:
a collimating lens configured to collimate illumination of the primary illumination beam.

9. The illumination apparatus of claim 1, wherein the substrate comprises:
one or more semiconductor wafers.

10. An inspection system comprising:
an illumination source for generating a primary beam of illumination directed along a primary illumination direction;
one or more polarized illumination deflection elements positioned within the primary beam of illumination, the one or more illumination deflection elements configured to direct a first portion of the primary beam of illumination having a first polarization along a first illumination direction in order to form a first inspection beam, the one or more illumination deflection elements further configured to direct a second portion of the primary beam having a second polarization orthogonal to the first polarization along a second illumination direction in order to form a second inspection beam, the second illumination direction different from the first illumination direction; and
an objective configured to focus the first inspection beam having the first polarization onto a first region of a substrate, the objective further configured to focus the second inspection beam having the second polarization onto a second region of the substrate, the first region being spatially separated from the second region;
a first image sensor configured to image the first region of the substrate by collecting illumination from the substrate in response to the first inspection beam; and
a second image sensor different from the first image sensor and configured to image the second region of the substrate by collecting illumination from the substrate in response to the second inspection beam, the first image sensor and the second image sensor positioned in a common image plane of the inspection system, wherein the illumination collected by the first image sensor is non-interfering with the illumination collected by the second image sensor.

11. A method comprising:
generating a primary beam of illumination directed along a primary illumination direction;
directing a first portion of the primary beam of illumination having a first polarization along a first illumination direction with one or more actuatable polarized illumination deflection elements in order to form a first inspection beam;
directing a second portion of the primary beam of illumination having a second polarization orthogonal to the first polarization along a second illumination direction different from the first illumination direction with the one or more actuatable polarized illumination deflection elements in order to form a second inspection beam;
focusing the first inspection beam having a first polarization onto a first inspection region of the substrate; and
focusing the second inspection beam having a second polarization onto a second inspection region of the substrate being spatially separated from the first inspection region;
collecting illumination from the first region of the substrate in response to the first inspection beam;
collecting illumination from the second region of the substrate in response to the second inspection beam, wherein the illumination collected from the first region of the substrate is non-interfering with the illumination collected from the second region of the substrate.

* * * * *